United States Patent
Taylor

(10) Patent No.: US 7,485,090 B2
(45) Date of Patent: *Feb. 3, 2009

(54) SURGICAL DEVICES FOR IMPOSING A NEGATIVE PRESSURE TO STABILIZE CARDIAC TISSUE DURING SURGERY

(75) Inventor: Charles S. Taylor, San Francisco, CA (US)

(73) Assignee: MAQUET Cardiovascular LLC, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/946,596

(22) Filed: Sep. 21, 2004

(65) Prior Publication Data

US 2005/0038316 A1 Feb. 17, 2005

Related U.S. Application Data

(60) Continuation of application No. 10/020,451, filed on Dec. 14, 2001, now Pat. No. 6,893,391, which is a continuation of application No. 09/440,106, filed on Nov. 15, 1999, now Pat. No. 6,852,075, which is a division of application No. 08/870,687, filed on Jun. 6, 1997, now Pat. No. 6,032,672, which is a division of application No. 08/603,328, filed on Feb. 20, 1996, now Pat. No. 5,727,569.

(51) Int. Cl.
  *A61F 2/00* (2006.01)
  *A61F 13/00* (2006.01)
  *A47J 45/00* (2006.01)
  *A61B 19/00* (2006.01)

(52) U.S. Cl. .................... 600/37; 294/64.1; 128/897; 128/898

(58) Field of Classification Search .............. None
See application file for complete search history.

(56) References Cited

U.S. PATENT DOCUMENTS 452,131 A 5/1891 Haughawout (Continued)

FOREIGN PATENT DOCUMENTS

DE 31 38 589 A1 4/1983

(Continued)

OTHER PUBLICATIONS

Akins, et al. "Preservation of interventricular septal function in patients having coronary artery bypass grafts without cardiopulmonary bypass," *American Heart Journal*, (1984) vol. 107(2): 304-309.

(Continued)

*Primary Examiner*—Robert L Nasser
(74) *Attorney, Agent, or Firm*—Alan W. Cannon; Law Office of Alan W. Cannon

(57) ABSTRACT

The invention is devices and techniques which use a negative (suction) pressure or vacuum, applied through a surgical instrument, to fix the position of a portion of the surface of a beating heart so that a surgical procedure can be more easily performed. The devices apply a negative pressure at several points on the outer surface of the heart such that a portion of the heart is fixed in place by the suction imposed through the surgical instrument. Because the instrument fixes the position of the tissue, and because the instruments remain at a constant distance from the particular portion of the heart where the surgery is being performed, the device may also serve as a support or platform so that other surgical instruments or devices can be advantageously used at the site. In certain preferred embodiments, the devices described herein have structures to facilitate the use of additional surgical instruments such that the placement of negative pressure device permit the surgeon to advantageously manipulate the other instruments during surgery. The negative pressure is preferably imposed through a plurality of ports which may be disposed in a substantially planar surface of the instrument which contacts the cardiac tissue.

41 Claims, 7 Drawing Sheets

U.S. PATENT DOCUMENTS

| | | |
|---|---|---|
| 810,675 A | 1/1906 | Richter |
| 1,706,500 A | 3/1929 | Smith |
| 2,082,782 A | 6/1937 | Allen |
| 2,296,793 A | 9/1942 | Kirschbaum |
| 2,590,527 A | 3/1952 | Fluck |
| 2,693,795 A | 11/1954 | Grieshaber |
| 2,863,444 A | 12/1958 | Winsten |
| 3,361,133 A | 1/1968 | Kimberly et al. |
| 3,392,722 A | 7/1968 | Jorgensen |
| 3,466,079 A | 9/1969 | Mammel |
| 3,584,822 A | 6/1971 | Oram |
| 3,683,926 A | 8/1972 | Suzuki |
| 3,720,433 A | 3/1973 | Rosfelder |
| 3,783,873 A | 1/1974 | Jacobs |
| 3,807,406 A | 4/1974 | Rafferty et al. |
| 3,858,926 A | 1/1975 | Ottenhues |
| 3,882,855 A | 5/1975 | Shulte et al. |
| 3,912,317 A | 10/1975 | Ohnaka et al. |
| 3,916,909 A | 11/1975 | Kletschka et al. |
| 3,983,863 A | 10/1976 | Janke et al. |
| 4,047,532 A | 9/1977 | Phillips et al. |
| 4,048,987 A | 9/1977 | Hurson |
| 4,049,000 A | 9/1977 | Williams |
| 4,049,002 A | 9/1977 | Kletschka et al. |
| 4,049,484 A | 9/1977 | Priest et al. |
| 4,050,465 A | 9/1977 | Perisse |
| 4,052,980 A | 10/1977 | Grams et al. |
| 4,053,953 A | 10/1977 | Flom et al. |
| 4,094,484 A | 6/1978 | Galione et al. |
| 4,096,853 A | 6/1978 | Weigand |
| 4,096,864 A | 6/1978 | Kletschka et al. |
| 4,217,890 A | 8/1980 | Owens |
| 4,226,228 A | 10/1980 | Shin et al. |
| 4,230,119 A | 10/1980 | Blum |
| 4,300,564 A | 11/1981 | Furihata |
| 4,306,561 A | 12/1981 | de Medinaceli |
| 4,350,160 A | 9/1982 | Kolesov et al. |
| 4,366,819 A | 1/1983 | Kaster |
| 4,368,736 A | 1/1983 | Kaster |
| 4,421,107 A | 12/1983 | Estes et al. |
| 4,423,728 A | 1/1984 | Lieberman |
| 4,428,368 A | 1/1984 | Torii |
| 4,434,791 A | 3/1984 | Darnell |
| 4,457,300 A | 7/1984 | Budde |
| 4,461,284 A | 7/1984 | Fackler |
| 4,492,229 A | 1/1985 | Grunwald |
| 4,597,382 A | 7/1986 | Perez, Jr. |
| 4,617,916 A | 10/1986 | LeVahn et al. |
| 4,627,421 A | 12/1986 | Symbas et al. |
| 4,637,377 A | 1/1987 | Loop |
| 4,646,747 A | 3/1987 | Lundback |
| 4,688,570 A | 8/1987 | Kramer et al. |
| 4,702,230 A | 10/1987 | Pelta |
| 4,708,510 A | 11/1987 | McConnell et al. |
| D293,470 S | 12/1987 | Adler |
| 4,718,418 A | 1/1988 | L'Esperance, Jr. |
| 4,726,356 A | 2/1988 | Santilli et al. |
| 4,726,358 A | 2/1988 | Brady |
| 4,736,749 A | 4/1988 | Lundback |
| 4,747,395 A | 5/1988 | Brief |
| 4,754,746 A | 7/1988 | Cox |
| 4,803,984 A | 2/1989 | Narayanan et al. |
| 4,808,163 A | 2/1989 | Laub |
| 4,827,926 A | 5/1989 | Carol |
| 4,829,985 A | 5/1989 | Couetil |
| 4,841,967 A | 6/1989 | Chang et al. |
| 4,852,552 A | 8/1989 | Chaux |
| 4,854,318 A | 8/1989 | Solem et al. |
| 4,858,552 A | 8/1989 | Glatt et al. |
| 4,863,133 A | 9/1989 | Bonnell |
| 4,865,019 A | 9/1989 | Phillips |
| 4,884,559 A | 12/1989 | Collins |
| 4,904,012 A | 2/1990 | Nishiguchi et al. |
| 4,925,443 A | 5/1990 | Heilman et al. |
| 4,949,707 A | 8/1990 | LeVahn et al. |
| 4,949,927 A | 8/1990 | Madocks et al. |
| 4,955,896 A | 9/1990 | Freeman |
| 4,957,477 A | 9/1990 | Lundback |
| 4,962,758 A | 10/1990 | Lasner et al. |
| 4,971,037 A | 11/1990 | Pelta |
| 4,973,300 A | 11/1990 | Wright |
| 4,989,587 A | 2/1991 | Farley |
| 4,991,578 A | 2/1991 | Cohen |
| 4,993,862 A | 2/1991 | Pelta |
| 4,997,437 A | 3/1991 | Grieshaber |
| 5,009,660 A | 4/1991 | Clapham |
| 5,011,469 A | 4/1991 | Buckberg et al. |
| 5,011,498 A | 4/1991 | Krumeich et al. |
| 5,019,086 A | 5/1991 | Neward |
| 5,025,779 A | 6/1991 | Bugge |
| 5,036,868 A | 8/1991 | Berggren et al. |
| 5,037,428 A | 8/1991 | Picha et al. |
| 5,052,373 A | 10/1991 | Michelson |
| 5,053,041 A | 10/1991 | Ansari et al. |
| 5,071,412 A | 12/1991 | Noda |
| 5,080,088 A | 1/1992 | LeVahn |
| 5,085,657 A | 2/1992 | Ben-Simhon |
| 5,098,369 A | 3/1992 | Heilman et al. |
| 5,107,852 A | 4/1992 | Davidson et al. |
| 5,119,804 A | 6/1992 | Anstadt |
| 5,125,395 A | 6/1992 | Adair |
| 5,131,905 A | 7/1992 | Grooters |
| 5,133,724 A | 7/1992 | Wilson, Jr. et al. |
| 5,139,517 A | 8/1992 | Corral |
| 5,150,706 A | 9/1992 | Cox et al. |
| 5,152,777 A | 10/1992 | Goldberg et al. |
| 5,159,921 A | 11/1992 | Hoover |
| RE34,150 E | 12/1992 | Santilli et al. |
| 5,167,223 A | 12/1992 | Koros et al. |
| 5,171,254 A | 12/1992 | Sher |
| 5,192,070 A | 3/1993 | Nagai et al. |
| 5,196,003 A | 3/1993 | Bilweis |
| 5,213,570 A | 5/1993 | VanDeripe |
| 5,231,974 A | 8/1993 | Giglio et al. |
| 5,256,132 A | 10/1993 | Snyders |
| 5,268,640 A | 12/1993 | Du et al. |
| 5,287,861 A | 2/1994 | Wilk |
| 5,290,082 A | 3/1994 | Palmer et al. |
| 5,293,863 A | 3/1994 | Zhu et al. |
| 5,300,087 A | 4/1994 | Knoepfler |
| 5,318,013 A | 6/1994 | Wilk |
| 5,336,252 A | 8/1994 | Cohen |
| 5,348,259 A | 9/1994 | Blanco et al. |
| 5,363,882 A | 11/1994 | Chikama |
| 5,382,756 A | 1/1995 | Dagan |
| 5,383,840 A | 1/1995 | Heilman et al. |
| 5,403,335 A | 4/1995 | Loomas et al. |
| 5,417,709 A | 5/1995 | Slater |
| 5,425,705 A | 6/1995 | Evard et al. |
| 5,437,651 A | 8/1995 | Todd et al. |
| 5,452,733 A | 9/1995 | Sterman et al. |
| 5,453,078 A | 9/1995 | Valentine et al. |
| 5,467,763 A | 11/1995 | McMahon et al. |
| 5,480,425 A | 1/1996 | Ogilive |
| 5,484,391 A | 1/1996 | Buckman, Jr. et al. |
| 5,498,256 A | 3/1996 | Furnish |
| 5,503,617 A | 4/1996 | Jako |
| 5,509,890 A | 4/1996 | Kazama |
| 5,512,037 A | 4/1996 | Russell et al. |
| 5,514,075 A | 5/1996 | Moll et al. |
| 5,514,076 A | 5/1996 | Ley |
| 5,520,610 A | 5/1996 | Giglio et al. |
| 5,522,819 A | 6/1996 | Graves et al. |
| 5,527,569 A | 6/1996 | Hobson et al. |

| | | |
|---|---|---|
| 5,529,571 A | 6/1996 | Daniel |
| 5,536,251 A | 7/1996 | Evard et al. |
| 5,547,458 A | 8/1996 | Ortiz et al. |
| 5,569,274 A | 10/1996 | Rapacki et al. |
| 5,571,074 A | 11/1996 | Buckman, Jr. et al. |
| 5,571,215 A | 11/1996 | Sterman et al. |
| 5,573,496 A | 11/1996 | McPherson et al. |
| 5,582,580 A * | 12/1996 | Buckman et al. ............... 601/41 |
| 5,607,421 A | 3/1997 | Jeevanandam et al. |
| 5,607,446 A | 3/1997 | Beehler et al. |
| 5,613,937 A | 3/1997 | Garrison et al. |
| 5,632,746 A | 5/1997 | Middleman et al. |
| 5,651,378 A | 7/1997 | Metheny et al. |
| 5,662,300 A | 9/1997 | Michelson |
| 5,667,480 A | 9/1997 | Knight et al. |
| 5,713,951 A | 2/1998 | Garrison et al. |
| 5,727,569 A | 3/1998 | Benetti et al. |
| 5,728,151 A | 3/1998 | Garrison et al. |
| 5,730,757 A | 3/1998 | Benetti et al. |
| 5,735,290 A | 4/1998 | Sterman et al. |
| 5,749,892 A | 5/1998 | Vierra et al. |
| 5,755,660 A | 5/1998 | Tyagi |
| 5,766,151 A | 6/1998 | Valley et al. |
| 5,772,583 A | 6/1998 | Wright et al. |
| 5,782,746 A | 7/1998 | Wright |
| 5,795,291 A | 8/1998 | Koros et al. |
| 5,797,960 A | 8/1998 | Stevens et al. |
| 5,799,661 A | 9/1998 | Boyd et al. |
| 5,807,243 A | 9/1998 | Vierra et al. |
| 5,813,410 A | 9/1998 | Levin |
| 5,818,231 A | 10/1998 | Smith |
| 5,836,311 A | 11/1998 | Borst et al. |
| 5,864,275 A | 1/1999 | Ohashi et al. |
| 5,888,247 A | 3/1999 | Benetti |
| 5,891,017 A | 4/1999 | Swindle et al. |
| 5,894,843 A | 4/1999 | Benetti et al. |
| 5,906,607 A | 5/1999 | Tayler |
| 5,927,284 A | 7/1999 | Borst et al. |
| 6,015,378 A | 1/2000 | Borst et al. |
| 6,032,672 A | 3/2000 | Taylor |
| 6,110,187 A | 8/2000 | Donlon |
| 6,139,492 A | 10/2000 | Vierra et al. |
| 6,149,583 A | 11/2000 | Vierra et al. |
| 6,183,486 B1 | 2/2001 | Snow et al. |
| 6,315,717 B1 | 11/2001 | Benetti et al. |
| 6,328,688 B1 | 12/2001 | Borst et al. |
| 6,334,843 B1 | 1/2002 | Borst et al. |
| 6,336,898 B1 | 1/2002 | Borst et al. |
| 6,346,077 B1 | 2/2002 | Taylor et al. |
| 6,350,229 B1 | 2/2002 | Borst et al. |
| 6,364,826 B1 | 4/2002 | Borst et al. |
| 6,371,906 B1 | 4/2002 | Borst et al. |
| 6,394,948 B1 | 5/2002 | Borst et al. |
| 6,394,951 B1 | 5/2002 | Taylor et al. |
| 6,464,630 B1 | 10/2002 | Borst et al. |
| 6,478,029 B1 | 11/2002 | Boyd et al. |
| 6,482,151 B1 | 11/2002 | Vierra et al. |
| 6,494,211 B1 | 12/2002 | Boyd et al. |
| 6,852,075 B1 | 2/2005 | Taylor |

FOREIGN PATENT DOCUMENTS

| | | |
|---|---|---|
| DE | 9004513 | 6/1990 |
| DE | 41 39 695 A1 | 6/1993 |
| EP | 0 293 760 A2 | 12/1988 |
| EP | 0 293 760 A3 | 12/1988 |
| EP | 0 293 760 B1 | 12/1988 |
| EP | 0 630 629 A1 | 5/1994 |
| EP | 0 668 058 A1 | 8/1995 |
| GB | 168216 | 9/1921 |
| GB | 2 233 561 A | 1/1991 |
| GB | 2 267 827 A | 12/1993 |
| SU | 938967 | 7/1982 |

| | | | | |
|---|---|---|---|---|
| WO | WO 87/04081 | 7/1987 | | |
| WO | WO 88/00481 | 1/1988 | | |
| WO | WO 94/14383 | 7/1994 | | |
| WO | WO 94/18881 | 9/1994 | | |
| WO | WO 95/01757 | 1/1995 | | |
| WO | 95/17128 | * 6/1995 | ................. | 600/37 |
| WO | WO 95/15715 | 6/1995 | | |
| WO | WO 95/17127 | 6/1995 | | |
| WO | WO 96/00033 | 1/1996 | | |
| WO | WO 97/10753 | 3/1997 | | |

OTHER PUBLICATIONS

Ancalmo, et al. "A modified sternal retractor," *Ann. Thorac. Surg.*, (1976) vol. 21: 174.

Angelini, et al. "A fiber-optic retractor for harvesting the internal mammary artery," *Ann. Thorac. Surg.*, (1990) vol. 50: 314-315.

Angelini, et al. "A simple, inexpensive method of heart retraction during coronary artery bypass surgery," *Ann. Thora. Surg.*, (1988) vol. 46: 46-247.

Ankeney, et al. "To use or not to use the pump oxygenator in coronary bypass operations," *The Annals of Thoracic Surgery*, (1975) vol. 19(1): 108-109.

Anstadt, et al. "Direct mechanical ventricular actuation for cardiac arrest in humans," *Chest*, (1991) vol. 100(1): 86-92.

Antinori, et al. "A method of retraction during reoperative coronary operations using the favaloro retractor," *The Society of Thoracic Surgeons*, (1989).

Archer, et al. "Coronary artery revascularization without cardiopulmonary bypass," *Texas Heart Institute Journal*, (1984) vol. 11(1): 52-57.

Arom, et al. "Mini-sternotomy for coronary artery bypass grafting," *The Annals of Thoracic Surgery*, (1996) vol. 61: 1271-1272.

Ballantyne, et al. "Delayed recovery of severly 'stunned' myocardium with the support of a left ventricular assist device after coronary artery bypass graft surgery," *Journal of the American College of Cardiology*, (1987) vol. 10(3): 710-712.

Bedellino, et al. "The cardiac rag—Simple exposure of the heart," *Texas Heart Institute Journal*, (1988) vol. 15(2): 134-135.

Beg, et al. "Internal mammary retractor," *Ann Thorac, Surg.*, (1985) vol. 39(1): 286-287.

Benetti, et al. "Direct coronary surgery with saphenous vein bypass without either cardiopulmonary bypass graft or cardiac arrest," *The Journal of Cardiovascular Surgery*, (1985) vol. 26(3): 217-222.

Benetti, et al. "Direct myocardial revascularization without extracorporeal circulation," *Chest*, (1991) vol. 100(2): 312-316.

Benetti. "Coronary revascularization with arterial conduits via a small thoracotomy and assisted by thoracoscopy, although without cardiopulmonary bypass," *Cor Europaeum*, (1995) vol. 4(1): 22-24.

Borst, et al. "Regional cardiac wall immunobilization for open chest and closed Chest coronary artery bypass grafting on the beating heart: The 'octopus' method," *Circulation*, (1995) vol. 92(8 supp. I): I-177.

Borst, et al. "Coronary artery bypass grafting without cardiopulmonary bypass and without interruption of native coronary flow using a novel anastomosis site restraining device (octopus)", *J Am. Coll. Cardiol.*, (1996) vol. 27(6): 1356-1364.

Bugge. "A new internal mammary artery retractor," *Thorac. Cardiovasc Surgeon*, (1990) vol. 38: 316-317.

Buffolo, et al. "Direct myocardial revascularization without cardiopulmonary bypass," *Thorac. Cardiovasc. Surgeon*, (1985) vol. 33: 26-29.

Calafiore, et al. "Minimally invasive coronary artery bypass grafting," *The Annals of Thoracic Surgery*, (1996) vol. 62: 1545-1548.

Calvin, et al. "Circumflex exposure using a cardiac sling," *Ann Thorac Surg*, (1990 vol. 49: 833-834.

Campalani, et al. "A new self-retaining internal mammary artery retractor," *J. Cardiovas. Surg.*, (1987) vol. 28: 347-348.

Chaux, et al. "A new concept in sternal retraction: Applications for internal mammary artery dissection and valve replacement surgery," *Ann. Thorac. Surg.*, (1986) vol. 42: 473-474.

Cohen, et al. "Mini-sternotomy for coronary artery bypass grafting," *The Annals of Thoracic Surgery*, (1996) vol. 62: 1884-1885.

Cutler, et al. "New use for an old clamp," *Archives of Surgery*, (1980) vol. 115: 1136-1137.

Delacroix-Chevalier. "Surgical instruments," *IMA Saving Packages Brochure*.

Delrossi, et al. "A new retractor to aid in coronary artery surgery," *The Annals of Thoracic Surgery*, (1983) vol. 36(1): 101-102.

Fanning, et al. "Reoperative coronary artery bypass grafting without cardiopulmonary bypass," *The Annals of Thoracic Surgery*, (1993) vol. 55(2): 486-489.

Favaloro, et al. "Direct myocardial revascularization by saphenous vein graft," *The Annals of Thoracic Surgery*, (1970) vol. 10(2): 97-111.

Fonger, et al. "Enhanced preservation of acutely ischmenic myocardium with transeptal left ventricular assist," *The Annals of Thoracic Surgery*, (1994) vol. 57(3): 570-575.

Gacioch, et al. "Cardiogenic shock complicating acute myocardial infarction: The use of coronary angioplasty and the integration of the new support device into patient management," *Journal of the American College of Cardiology*, (1992) vol. 19(3).

Green. "Technique of internal mammary-coronary artery anastomosis," *The Journal of Cardiovascular Surgery*, (1979) vol. 78: 455-479.

Guzman. "Transient radial nerve injury related to the use of a self retraining retractor for internal mammary artery dissection," *J. Cardiovasc. Surg.*, (1989) vol. 30: 1015-1016.

Hasan, et al. "Technique of dissecting the internal mammary after using the moussalli bar," *European Journal of Cardio Thoracic Surgery*, (1990) vol. 4: 571-72.

Itoh, et al. "New modification of a mammary artery retractor," *Ann. Thorac. Surg.*, (1994) vol. 57:1670-1671.

*Japanese Journal of Thoracic Surgery*, (1989) vol. 42(2).

Japanese Article "Heart Retractor".

Janke. "Heart support for coronary bypass surgery involving the circumflex artery system," *The Journal of Thoracic and Cardiovascular Surgery*, pp. 883-884.

Kolessov. "Mammary artery-coronary artery anastomosis as method of treatment for angina pectoris," *Thoracic and Cardiovascular Surgery*, (1967) vol. 54(4): 535-544.

Kazama, et al. "Fabric heart retractor for coronary artery bypass operations," *The Annals of Thoracic Surgery*, (1993) vol. 55: 1582-1583.

Kresh, et al. "Heart-mechanical assist device interaction," *Trans. Am. Soc. Artif. Intern. Organs*, (1986) vol. 32: 437-443.

Lavergne, et al. "Transcatheter radiofrequency ablation of atrial tissue using a suction catheter," *PACE*, (1989) vol. 12(Part II): 177-186.

Lonn, et al. "Coronary artery operation supported by the hemopump: An experimental study on pigs," *The Annals of Thoracic Surgery*, (1994) vol. 58(1): 516-523.

Matsuura, et al. "A new device for exposing the circumflex coronary artery," *The Annals of Thoracic Surgery*, (1995) vol. 59: 1249-1250.

McGee, et al. "Extended clinical support with an implantable left ventricular assist device," *Trans. Am. Soc. Artif. Intern. Organs*, (1989) vol. 35: 614-616.

McKeown, et al. "A modified sternal retractor for exposure of the internal mammary artery," *Ann. Thorac. Surg.*, (1981) vol. 32: 619.

Ochsner, et al. "Surgical management of diseased intracavitary coronary arteries," *The Annals of Thoracic Surgery*, (1984) vol. 38(4): 356-362.

Parsonnet, et al. "Graduated probes for coronary bypass surgery," *The Journal of Thoracic and Cardiovascular Surgery*, (1974) vol. 68(3): 424-426.

Parsonnet, et al. "Self-retaining epicardial retractor for aortocoronary bypass surgery," *The Journal of Thoracic and Cardiovascular Surgery*, (1979): 629-630.

Pfister, et al. "Coronary artery bypass without cardiopulmonary bypass," *The Annals of Thoracic Surgery*, (1992) vol. 54(6): 1085-1092.

Phillips, et al. "A versatile retractor for use in harvesting the internal mammary artery and performing standard cardiac operations," *J. Thorac. Cardiovasc. Surg.*, (1989) vol. 97: 633-635.

"Pilling surgical instruments", *A Rusch International Company Brochure*.

Pittman, et al. "Improved visualization of the internal mammary artery with a new retractor system," *Ann. Thorac. Surg.*, (1989) vol. 48: 869-870.

Riahi, et al. "A simple technique and device to provide a bloodless operative field in coronary artery surgery without cross-clamping the aorta," *The Journal of Thoracic and Cardiovascular Surgery*, (1973) vol. 66(6): 974-978.

Richenbacher, et al. "Current status of cardiac surgery: A 40-year review," *Journal of American College of Cardiology*, vol. 14(3): 535-544.

Robicsek. "Aortic spoon-jaw clamp for aorta-saphenous vein anastomosis," *J. Card. Surg.*, (1995) vol. 10: 583-585.

Robinson, et al. "A minimally invasive surgical method for coronary revascularization—Preliminary experience in five patients," *Circulation*, (1995) vol. 92(8): 1-176.

Rousou, et al. "Cardiac retractor for coronary bypass operations," *Ann Thorac. Surg*, (1991) vol. 52: 877-878.

Roux, et al. "New helper instrument in cardiac surgery", *Ann. Thoracic Surgery*, (1989) vol. 48: 595-596.

Roux, et al. "Internal mammary artery dissection: A three dimensional sternal retractor," *J. Cardiovasc. Surg.*, (1989) vol. 30: 996-997.

Ruzevich, et al. "Long-term follow-up of survivors of postcardiotomy circulatory support," *Trans. Am. Soc. Artif. Intern. Organs*, (1988) vol. 34: 116-124.

Scholz, et al. "Transfemoral placement of the left ventricular assist device 'hemopump' during mechanical resuscitation," *Thoracic and Cardiovascular Surgeon*, (1990) vol. 38: 69-72.

Splittgerber, et al. "Exposing the circumflex coronary artery: The heartflip technique," *Ann Thorac Surg.*, (1996) vol. 61: 1019-1020.

Stevens, et al. "Closed chest coronary artery bypass with cardioplegic arrest in the dog," *67th Scientific Session*, 238, I-251.

Trapp, et al. "Placement of coronary artery bypass graft without pump oxygenator," *J. of the Society of Thoracic Surgeons and The Southern Thoracic Surgeons Assn.*, (1975) vol. 19(1).

USSC Cardiovascular Thora-Lift™, United States Surgical Corporation, Norwalk, Connecticut, Product Brochure.

Vincent. "A compact single post internal mammary artery dissection retractor," *Eur. J. Cardio-Thor. Surg.*, (1989) vol. 3: 276-277.

Westaby. "Coronary surgery without cardiopulmonary bypass," *British Heart Journal*, (1995) vol. 73: 203-205.

Westaby, et al. "Less invasive coronary surgery: Consensus from the oxford meeting," The *Annals of Thoracic Surgery*, (1996) vol. 62: 924-931.

Zumbro, et al. "A prospective evaluation of the pulsatile assist device," *The Annals of Thoracic Surgery*, (1979) vol. 28(2): 269-273.

\* cited by examiner

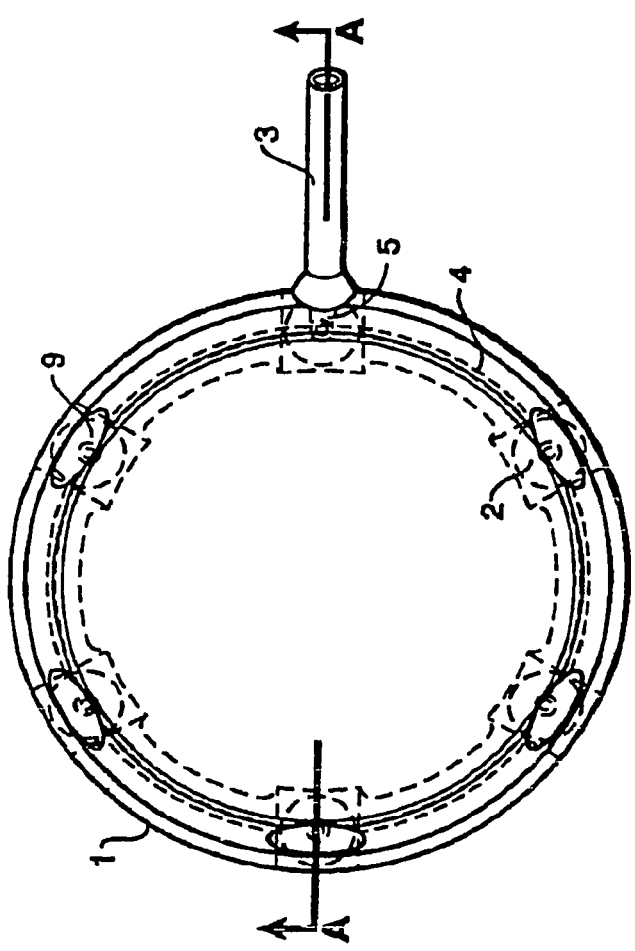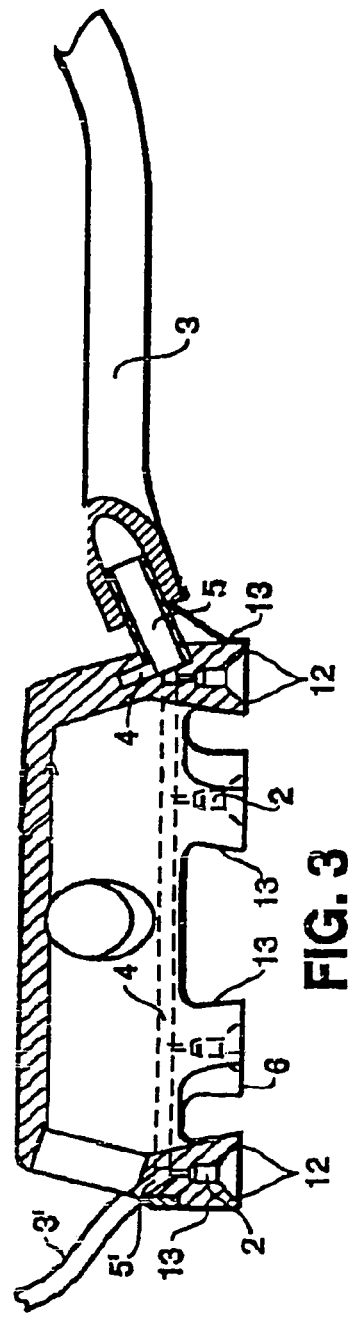
FIG. 1
FIG. 3

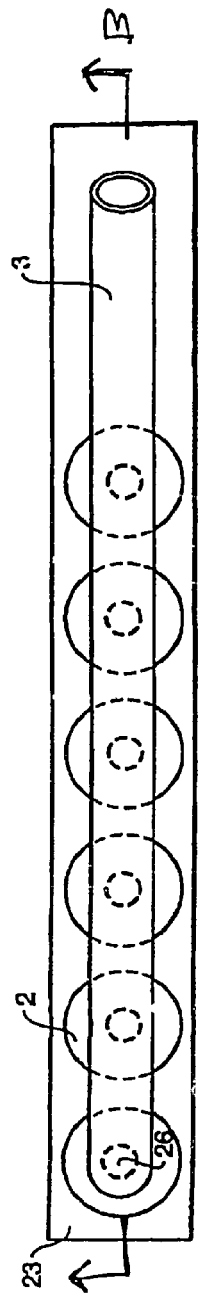
FIG. 6
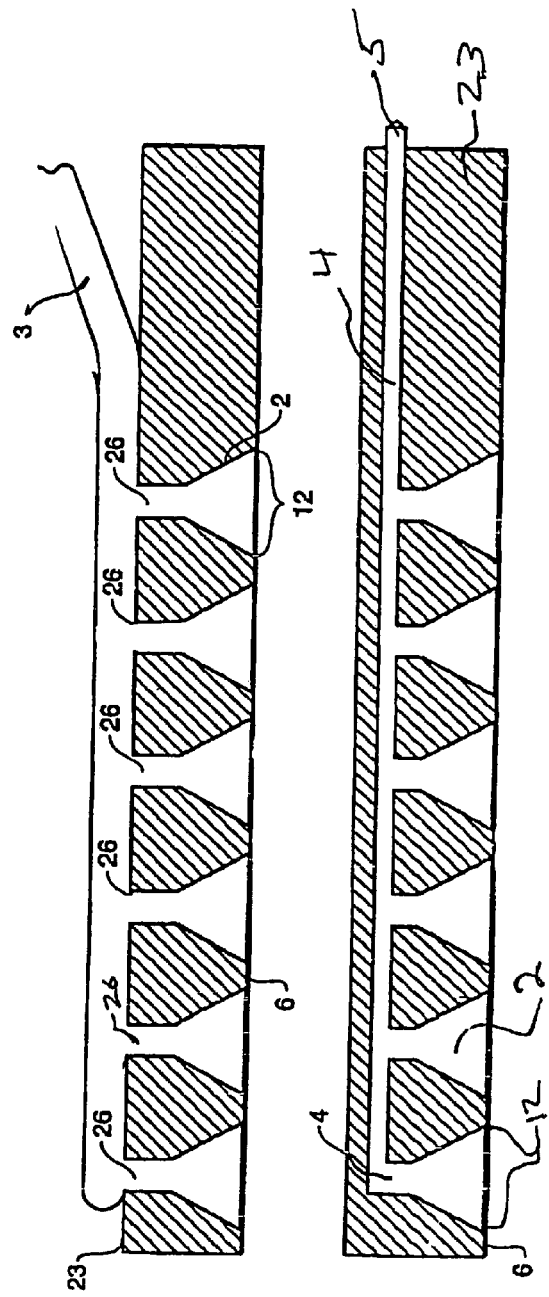
FIG. 7
FIG. 7a

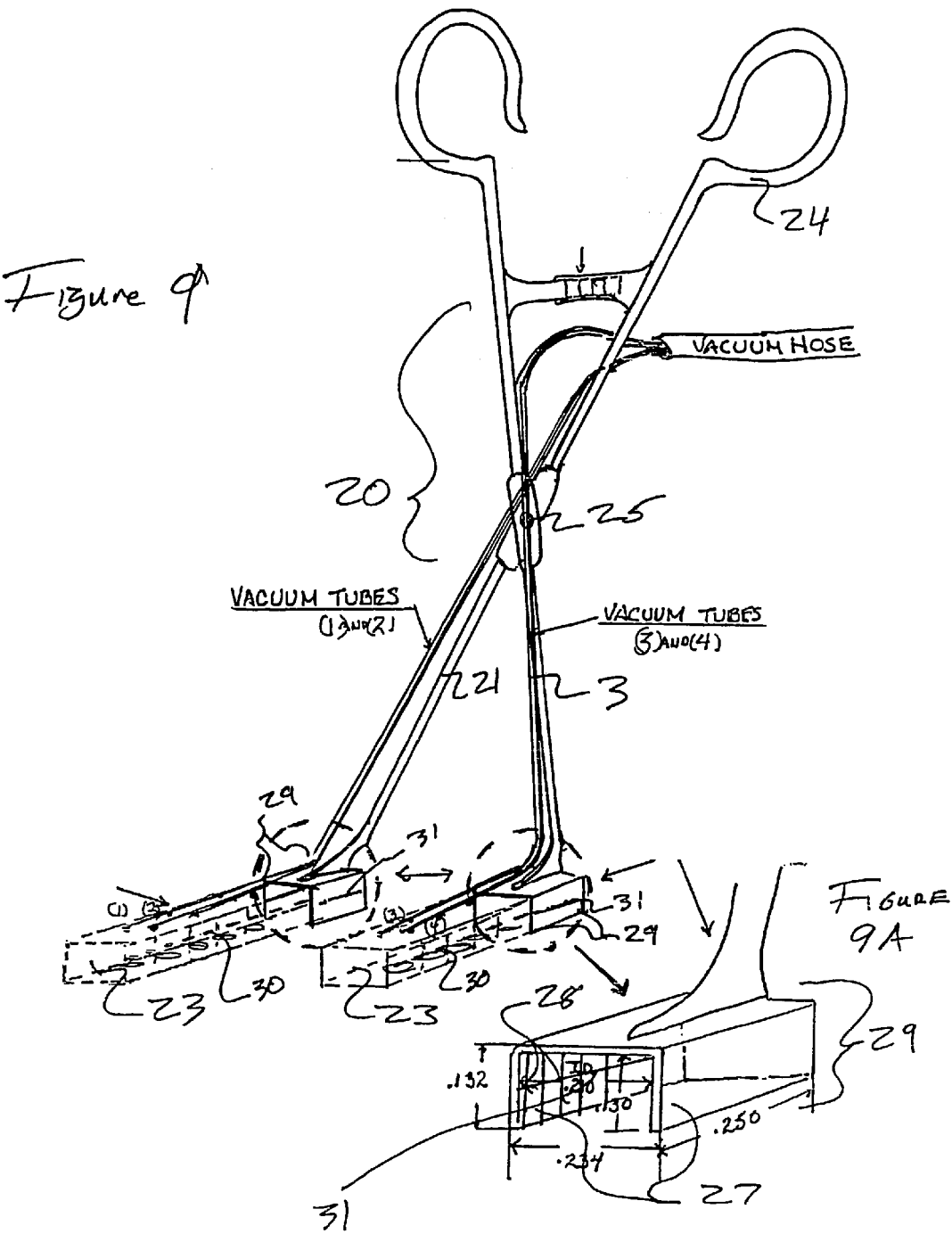

SURGICAL DEVICES FOR IMPOSING A NEGATIVE PRESSURE TO STABILIZE CARDIAC TISSUE DURING SURGERY

This application is a continuation of application Ser. No. 10/020,451 filed on Dec. 14, 2001, now U.S. Pat. No. 6,893, 391, which is a continuation of application Ser. No. 09/440, 106 filed on Nov. 15, 1999, now U.S. Pat. No. 6,852,075, which is a divisional of application Ser. No. 08/870,687 filed on Jun. 6, 1997, now U.S. Pat. No. 6,032,672, which is a divisional of application Ser. No. 08/603,328 filed on Feb. 20, 1996, now U.S. Pat. No. 5,727,569. The priority of the aforementioned application is expressly claimed and the applications and patents are hereby incorporated herein, in their entireties, by reference thereto.

Surgeries to treat disease in the heart, particularly blockages in coronary vessels, are becoming increasingly common and necessary to treat atherosclerosis and other conditions causing reduced blood flow to the heart. For many years, surgeons have performed "open-heart" surgery to repair defects in the heart and the associated cardiovascular system. As these procedures have become more common and more costly, a need has developed for techniques to make cardiac surgical procedures less traumatic to the patient. The necessity of attaching a surgical patient to a cardiopulmonary bypass (CPB) apparatus is a primary contribution to the trauma inherent in traditional procedures. To attempt to alleviate the trauma and side effects of CPB, surgeons have begun performing cardiac surgeries without stopping the heart. To successfully perform such surgery, several challenges must be met. One particular problem confronting the surgeon who operates on the beating heart is the difficulty in performing extremely delicate surgical procedures while the contractions of the heart muscles cause the surface of the heart to continuously move.

To attempt to restrict the motion of heart at the particular area where the surgeon is working, the surgeon may pass at least a pair of sutures through the exterior tissue layers of the heart. By pulling the sutures in opposite directions, the tissue is stretched, and the motion caused by the contractions of the heart muscles is reduced or partially compensated. This technique is not completely effective in preventing the natural motion of the heart and requires extra time to place the sutures, and, additionally, may cause damage to the cardiac tissue when the sutures are placed or manipulated. Preferably, the surgeon would be able to fix the motion of the cardiac tissue containing or adjacent to an area where surgery is to be performed without the need to attach or manipulate additional sutures. The ability to fix the position of the cardiac tissue in a region of the heart would permit the surgeon to perform delicate surgical procedures on the beating heart while the portion of the heart on which the surgery is performed remains substantially motionless throughout the procedure.

SUMMARY OF THE INVENTION

This invention is devices and techniques which use a negative pressure (vacuum) applied through a surgical instrument, to fix the position of a portion of the surface of a beating heart so that a surgical procedure can be more easily performed. The devices disclosed herein apply a negative pressure at several points on the outer surface of the heart such that a portion of the exterior tissue of the heart is fixed in place by the suction imposed through the surgical instrument. Because the negative pressure introduced through the instrument-s the position of a region of tissue, the instrument remains at a constant distance from the particular portion of the heart where the surgery is being performed. In this configuration, the device may also serve as a support or platform so that other surgical instruments or devices can be advantageously used at the site. In certain preferred embodiments, the devices described herein have structures to facilitate the use of additional surgical instruments such that the placement of the negative pressure instrument permits the surgeon to advantageously manipulate the other instruments used during the surgery.

The negative pressure is preferably imposed through a plurality of ports which may be disposed in a substantially planar surface of the instrument which contacts the cardiac tissue. The ports are preferably oriented such that the pressure is applied at several points over the target area to fix the position of the tissue and to reduce any trauma to the tissue caused by the negative pressure.

DESCRIPTION OF THE FIGURES

FIG. 1 is an embodiment of the invention having a substantially annular housing with a plurality of suction ports disposed about the periphery of the instrument and having openings in the bottom surface which contacts the heart.

FIG. 3 is a section of a substantially circular embodiment showing a preferred configuration for the suction ports and a pressure conducting chamber for introducing the negative pressure to each suction port.

FIG. 6 is a plurality of suction ports contained within a block having attached thereto a pair of vacuum lines for introducing a negative pressure to each suction port.

FIGS. 7 and 7A are sectional views of the block showing an alternate configuration for the suction ports and the pressure conducting space.

FIGS. 9 and 9A are a hand held instrument having a removable block, wherein the instrument has a receiving means to reversibly receive the block.

DETAILED DESCRIPTION OF THE INVENTION

Figure 2:
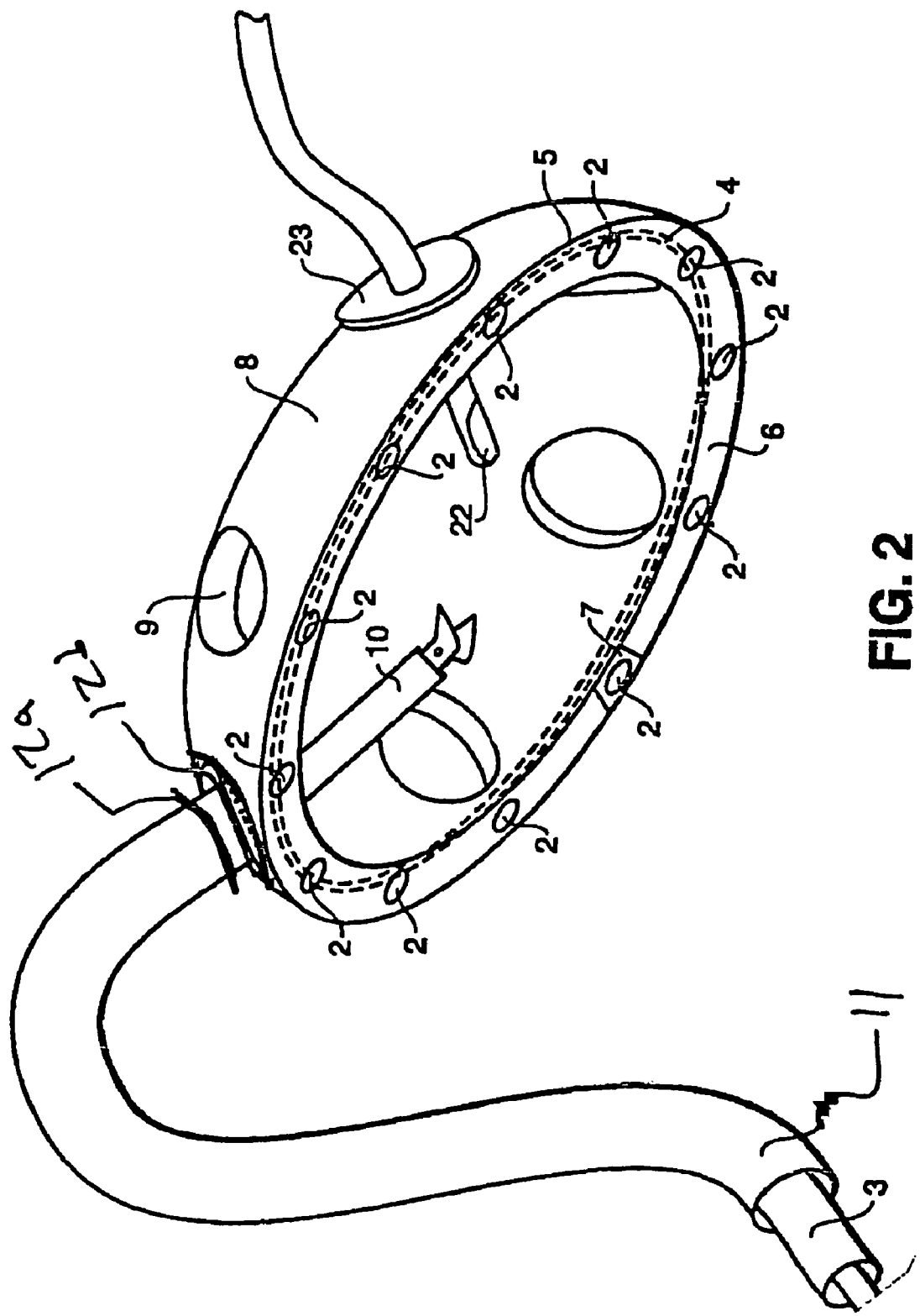
FIG. 2 is a dome-shaped or semi-spherical embodiment having a plurality of suction ports disposed about the periphery of the bottom surface and having several instrument ports in the dome portion through which additional surgical instruments may be introduced, positioned, or manipulated.

This invention is surgical instruments and techniques which advantageously apply a negative pressure to the surface of the heart so that a portion thereof is maintained at a fixed position during a surgical procedure. The negative pressure is introduced to the instrument and is applied at several points over the surface of the heart proximate to or surrounding the portion of the heart the position of which is desired to be fixed during the procedure. The instruments feature several suction ports which are brought into contact with the heart, followed by the application of a negative pressure through the instrument, to fix the position of the tissue based on the placement of the instrument. The instruments may also contain a sealed, airtight pressure conducting chamber for operably connecting to a pressure inlet for communicating the negative pressure to the suction ports. Alternatively, each suction port may have a dedicated vacuum line attached thereto.

The shape of the instrument may be varied depending on the particular application or the clinical diagnosis for an individual patient. In some embodiments, the shape of the instrument is defined by a housing forming a complete or partial, substantially annular, ring having the suction ports disposed about the periphery of the bottom surface of the housing. The suction ports are contained within the base of the instrument and the opening of the suction ports are contained in the bottom surface of the instrument which may be substantially planar or may be shaped to conform to the surface of the heart.

In another embodiment, the operative portion of the instrument may be defined by one or more arrays of suction ports which are substantially linear. The suction ports may be contained in a block which has at least one vacuum line attached thereto. This design is particularly suitable for an instrument having a shaft affixed thereto for positioning the block containing the suction ports. The shaft may be fixed to a rigid support during the procedure or may be part of a hand-held instrument having a handle structure adapted to be grasped by the human hand. In a preferred embodiment, the hand-held instrument contains a pair of shafts having a block and suction port assembly at each end thereof. The shafts are connected at an intermediate portion by a pivot which allows the suction port assemblies to move relative to one another, to be oriented and manipulated by hand, and to be locked into place in a desired configuration.

An embodiment having more than one movable member in which suction ports are contained offers the advantage that a negative pressure may be first imposed through the suction ports of each movable member to fix the tissue, followed by manipulation of the individual members which causes the tissue to be stretched or oriented such that one portion of the cardiac tissue is fixed in position by one movable member and can be oriented relative to another portion fixed by a second movable member.

The negative or vacuum pressure imposed may be varied depending on the design of the instrument, the orientation of the ports, and the amount of pressure needed to hold a particular region of the heart in place. When manipulating the instruments of this invention, it is not, desired to exert a downward force on the instrument once the instrument engages the cardiac tissue because the tissue could be damaged by being drawn into the suction ports, thus risking interruption of blood flow and ischemic or reperfusion injury to the cardiac tissue. However, once a negative pressure is imposed, the instrument may be drawn away from the heart such that the portion of the surface tissue fixed by the suction ports is slightly elevated relative to the remainder of the heart.

Referring to FIGS. 1 and 3, an embodiment of the invention is an instrument comprised of an annular housing 1 which could have an alternate shape depending on the design and clinical application of the instrument. For example, the body of the instrument has a housing which may be a portion of a circle, an oval, semi-oval, U-shape, or linear member. The portion of the housing 1 which contains the suction ports 2 has a bottom surface 6 which rests against the surface of the heart and therefore should be substantially planar or curved to the extent necessary to simultaneously bring the suction ports 2 into conforming contact with the heart. Referring to FIGS. 1 and 3, one embodiment of the invention has suction ports 2 equally spaced about the circumference of the housing 1. For purposes of stability, it is preferred that each suction port 2 be substantially equidistant from each adjacent port and spread over the entire portion of the instrument at the points of contact to the heart so that the instrument is more stably affixed to the surface of the heart when a negative pressure is imposed. As described in detail below, the housing 1 may also have one or more instrument ports 9 to facilitate introducing a surgical instrument to the site of the surgery to function on or in proximity to the fixed portion of the cardiac tissue.

The interior of the housing 1 may be further comprised of a means for introducing a negative pressure to the suction ports 2. For example, each suction port 2 may have a dedicated vacuum line 3 for introducing a negative pressure to each suction port 2. However, it is preferred that a single vacuum line 3 introduce the negative pressure via an inlet 5 which leads to an airtight, sealed, and pressure conducting chamber 4 contained within the annular housing 1 which in turn communicates the negative pressure to each suction port 2. Thus, by connecting a negative pressure source to the inlet 5, the negative pressure is introduced to the instrument through inlet 5, thereby creating a negative pressure in the pressure conducting chamber 4 which is communicated to each suction port 2. The housing may also have at least one instrument port 9 comprised of an opening that preferably traverses the width of the housing and is shaped to receive an instrument. In use, the surgeon may advantageously rely on the housing 1 as a platform for other instruments which may advantageously be used at the portion of the heart fixed in place by the negative pressure. The instrument port 9 may be a simple opening in the housing 1 or may be designed to operably receive a specific instrument as described in more detail below.

In use (See FIG. 4), the instrument is gently positioned on the surface of the heart by manipulating the position of the housing 1 such that each suction port 2 rests against the cardiac tissue. Once the instrument is positioned on the surface of the heart, the negative pressure is applied through vacuum line 3 and inlet 5 while the housing may be gently manipulated to insure that the negative pressure is causing the cardiac tissue to become fixed to each suction port 2. Once the suction ports become functionally attached to the surface of the heart, the portion of the surface of the heart becomes fixed relative to the instrument. Once the negative pressure is applied, the instrument may be attached to a stable support such as a rib retractor or other structure which does not move relative to the beating heart.

Referring to FIG. 2, a dome-shaped or semi-spherical embodiment of the invention has a plurality of suction ports 2 spaced about the periphery of the bottom surface 6 of the dome portion 8 such that the entire instrument is fixed to the cardiac tissue at the point of each of the several suction ports 2. As with the above embodiment, it is preferred that each suction port 2 be pneumatically connected via an air-tight pressure conduction chamber 4. The base of the instrument is comprised of a substantially flat bottom surface 6 wherein the opening of each of the suction ports 2 is flush at the bottom surface 6. The bottom surface 6 is preferably substantially flat because the bottom surface 6 will engage the surface of the heart when the negative pressure is imposed. Alternatively, depending upon the size of the instrument and the location of placement on the surface of the heart, the bottom surface 6 may be contoured so that the suction ports 2 may engage a curved surface of the heart. The bottom surface 6 may also have a separate contact layer to cushion the contact between the instrument and the heart tissue and to facilitate forming a tight seal when the negative pressure is imposed The contact layer may cover substantially the entire bottom surface 6 proximate to the openings of the suction ports 2. If the material surrounds the openings of the suction ports, it is preferable that the material not be air permeable to prevent the negative pressure from passing through the contact layer 7. Also, the contact layer 7 may be attached at the periphery of the bottom surface 6. The available materials for the contact layer 7 include the well-known and commercially available medial plastics such as TEFLON®, silicone, and others which are pliable and biocompatible.

The dome-shaped or semi-spherical embodiment of the invention advantageously has at least one instrument port 9 which may be placed in any of several locations but which is preferably located in the dome portion 8 of the apparatus. The instrument port 9 facilitates introducing the functional portion of an instrument 10 into the interior of the dome portion 8, such that the instrument 10 can perform any of several functions on the cardiac tissue. The instrument 10 could include a cutting apparatus, visual means, such as a scope or light, suturing instruments, suction, blowing, or irrigation apparatus or any like instrument used during a surgical procedure. Multiple instrument ports 9 disposed in the dome portion 8 allow several instruments 10 to be introduced to the surgical site from numerous directions and to be fixed in place relative to the heart.

The instrument ports 9 may be comprised of only a simple opening in the dome portion 8. Alternatively, the instrument ports 9 may also have a flexible or rigid shaft 11 or other attachment means fixed to the dome portion 8 to facilitate introducing an instrument or a member associated therewith such as wires, tubes, cables which comprise or are used to perform the function of the instrument 10. The shaft 11 may also comprise the inlet (not shown) for introducing negative pressure to the pressure conducting chamber 4. Because the dome portion 8 remains at a fixed distance to the heart, the instrument ports 9 or shaft 11 may have a collar 23 or stop associated therewith such that the distance between the instrument 10 and the heart can be predetermined and fixed by, for example, abutting a stop 12a on the instrument 10 against a stop 12b or collar on the instrument port 9.

The instrument ports may also contain a locking means which may be magnetic or suction-driven so that the instrument 10 can be locked into place on the dome-portion 8. For example, the surgeon may view the procedure via a scope 22 which communicates an image to a video monitor. This invention may be advantageously used to establish and maintain an optimal position for the scope by inserting the scope 22 through the instrument port and then fixing the position of the scope 22. The end of the scope 22 may have a collar 23 or other stop mechanism near its end, such that the scope 22 may be introduced through the instrument port 9 wherein the movement of the scope 22 toward the heart is terminated by the contact between the collar 23 of the scope 22 and the periphery of the instrument port 9.

Referring to FIG. 3, a sectional view through line A-A at FIG. 1 shows the interior of the pressure conducting chamber 4 and associated passages or conduits associated with the suction ports 2 such that the negative pressure in the pressure conducting chamber 4 is introduced from vacuum line 3, via inlet 5, and ultimately to the suction ports 2. The suction ports 2 have a substantially circular opening 12 disposed in the bottom surface 6. Although this embodiment has a single inlet 5 such that the pressure is introduced to each suction portion 2 via the pressure conducting chamber 4, one or more of the suction ports 2 may each have an independent inlet 5' for a separate vacuum line 3'.

As noted above, the suction ports 2 are disposed within a bottom surface 6 which is preferably substantially flat. As noted above, the bottom surface 6 of the housing 1 may be a continuous ring or other annular shape which contacts the heart about the entire periphery of housing 1, but may also be comprised of a plurality of individual bases 13 which contain the one or more suction ports 2 and which contact the heart at several independent points which may be co-planar or which may be adapted to the contours of the heart.

Figure 4:
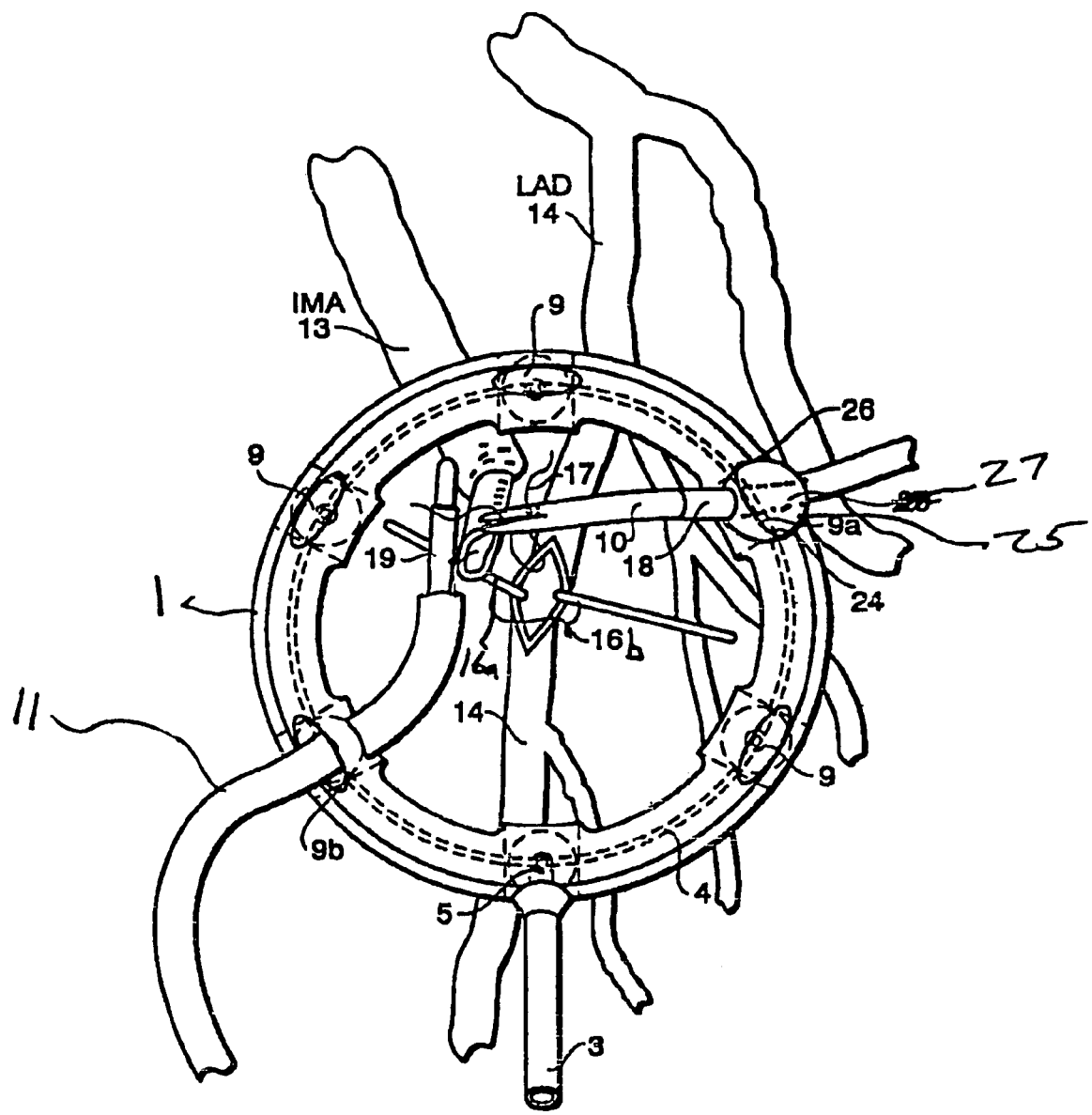
FIG. 4 is an embodiment of the instrument, in use, which is fixed on the surface of the heart and has additional surgical instruments operably associated therewith to facilitate a graft being inserted to form an anastomosis between the internal mammary artery (IMA) and the left anterior descending (LAD) artery.

Referring to FIG. 4, FIG. 4 shows an embodiment of the invention in use in a coronary artery bypass graft (CABG) procedure where an anastomosis is formed between the internal mammary artery IMA 13 and the left anterior descending artery LAD 14 and which is held open by vessel retractors 16a and 16b. One end of the anastomosis is sewn to the LAD 14 by sutures 17 being manipulated by instrument 10. A vacuum line 3 is attached to inlet 5, to introduce a negative pressure to the pressure conduction chamber 4. An instrument 10, which in this example is manipulating suture 17 for sewing the anastomosis at the LAD 14, is introduced via instrument port 9a located in the housing 1 of the apparatus. An instrument port 9a has a shaft 18 disposed within the instrument port 9a to facilitate positioning the instrument 10 relative to both the housing 1 and to the surgical site. The shaft 18 traverses all or a portion of the instrument port 9a and may be flexible such that the shaft 10 can be oriented in a fashion to direct the instrument 10 to the desired point within the surgical field. The shaft 18 may also be incorporated into a pivot 24 of any of several configuration including a ball 25 and socket 26 joint having a passage 27 running axially through the ball 25 wherein the shaft 18 is contained in the passage 27 such that the ball 25 is rotated within the socket 26 to rotate the instrument 10 about the pivot 24 to position the functional end of the instrument 10. An example of another instrument 19 is inserted through instrument port 9b by passing the instrument 19 through a rigid or flexible shaft 12 which is disposed within the instrument port 9b. In this example, the instrument 19 passes through the shaft 12 such that the position of the functional end of the instrument 19 is fixed. In the example shown in FIG. 4, the instrument 19 is being used to grasp the IMA 13 proximate to the attachment of the graft.

Figure 5:
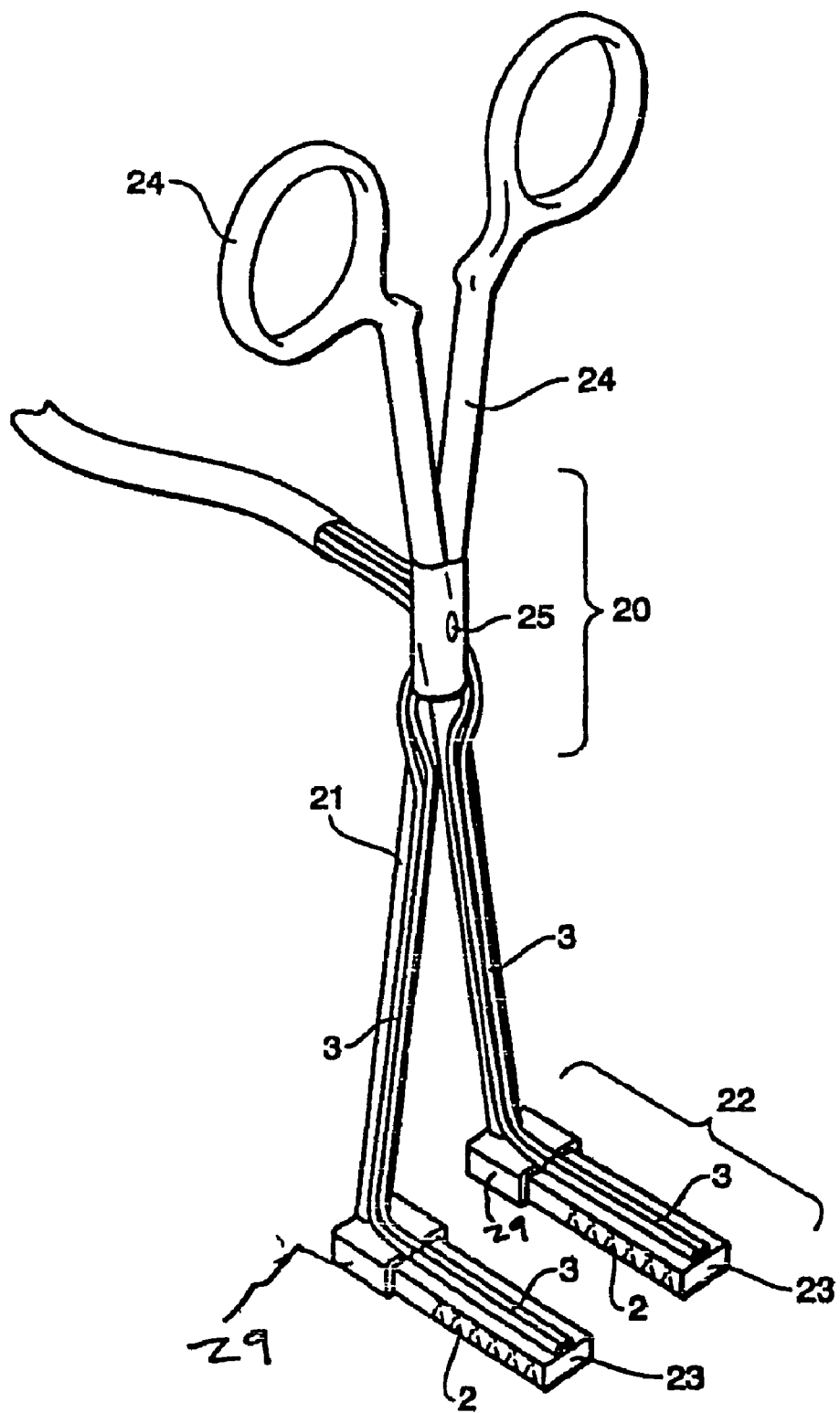
FIG. 5 is an alternative embodiment of the invention wherein the suction ports for imposing the negative pressure are affixed to a shaft which may be part of a hand-held device and are contained in a block where a plurality of individual suction ports are arranged in an array.

Referring to FIG. 5, pursuant to this invention, the suction ports 2 may be incorporated into a hand-held apparatus 20 having a shaft 21 attached to a suction part assembly 22 containing the suction ports 2, at least one vacuum line 3, and a block 23 wherein the suction ports 2 are contained. This embodiment may be operated by a surgeon or surgical assistant by hand grips 24 or the hand grips 24 may be replaced by a conventional attachment (not shown) for fixing the shaft 21 to a stable support such as a surgical retractor or other such fixed structure available during the surgical procedure. In a preferred embodiment, a pair of shafts 21 are interlinked by a pivot link 25 at an intermediate point in the shaft 21 such that each suction port assembly may be positioned independently of one another either before or after the negative pressure is applied. In this configuration, the cardiac tissue which is functionally attached to the instrument at the points of contact with the suction port assembly 22 may be drawn apart by imposing a negative pressure through the suction ports 2 and then manipulating the rigid shafts 21, or hand grips 24 of the instrument 20 such that each suction port assembly 22 is moved a distance from the other. The suction port assembly 22 is comprised of the block 23, in which the suction ports 2 are contained, and a receiving means 29 located at the terminal (lower) end at the shaft 21 which is shaped to receive the block 23 and to pen-nit introduction of the negative pressure from vacuum line 3 to the suction ports 2 contained within the block. The negative pressure is preferably, imposed by one or more vacuum lines 3 which may run parallel to the shaft 21 before terminating in the block 23 containing the suction ports 2 or at any convenient point in the suction port assembly 22. In a preferred embodiment, the blocks 23 are substantially rectangular structures wherein the suction parts 2 are placed in an array as described below.

Figure 8:
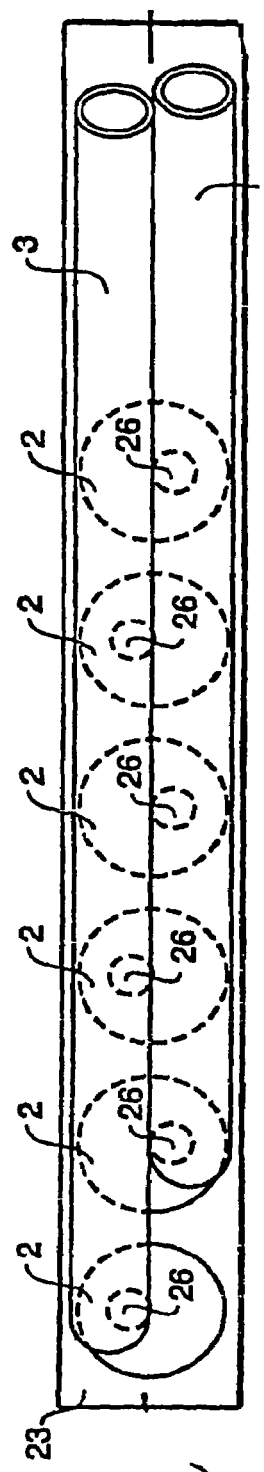
FIG. 8 is an alternative embodiment for an array of suction ports having vacuum tubes which run the length of the block and are oriented to be substantially perpendicular to a passage space leading to each suction port.

Referring to FIG. 6, the block 23 is comprised of a plurality of suction ports 2 which are connected to vacuum line 3 to create a negative pressure at each suction port 2. The number of individual vacuum lines 3 may be any number less than or equal to the number of suction ports 2. An individual suction port 2 may be connected to negative pressure via the pressure conducting space 4 (See FIG. 7A) or by a passage 26 which communicates an individual suction port 2 directly to the vacuum line 3. The passage 26 is preferably smaller in circumference than the opening of the suction port 2. In the embodiment of FIG. 6, every other suction port 2 is connected to either of two vacuum lines 3 which traverse substantially the length of the block 23. Alternatively, each suction port may also be connected to a single suction line as shown in FIG. 8. In the embodiment of FIG. 6, the passages 26 are oriented off-center to the circumference of the opening of the suction port 2. In a preferred embodiment, the block 23 is a separate molded rubber unit which is configured to fit reversibly into a receiving means 29 at the terminal end of the shaft 21. In this configuration, the suction port assembly 22 may be disassembled and the block 23 disposed after a single use.

Referring to FIG. 7, a sectional view of the block 23 through line B-B of FIG. 6 shows the suction ports 2 disposed with the block 23 in a linear array such that each suction port is equidistant from each adjacent suction port 2. The openings 12 of the suction ports 2 are flush with the bottom surface 6 of the block 23. In this embodiment, a pair of vacuum lines 3 connects each suction port 2 to negative pressure via a single passage 26 which runs from the vacuum line 3 to the suction port 2 and is substantially perpendicular to the vacuum line 3. Alternatively, as shown in FIG. 8, a single vacuum line 3 may connect each suction port 2 to negative pressure.

Referring to FIG. 7A, the block 23 may also have an inlet 5 which introduces the negative pressure to the suction ports 2. The suction ports 2 are disposed within the bottom surface 6 of the block 23 which is to be affixed to the end of the shaft 21 (see FIG. 5). As will be readily appreciated, the negative pressure can be introduced to the suction ports 2 by a variety of techniques as described above. The vacuum line 3 may be attached to the apparatus 20 at several points such as the individual suction ports as illustrated in FIG. 7 or via a single inlet 5 and communicated to each suction port 2 via pressure conducting space 4 (FIG. 7A) such that the negative pressure is introduced to the block 23 and communicated to each suction port 2. Thus, the objective of communicating the negative pressure to the suction ports 2 to fix the position of the cardiac tissue may be achieved via several alternate techniques which are based on or may be developed from the embodiments disclosed herein.

Referring to FIGS. 9 and 9A, as noted above the block 23 may be removable from the apparatus 20. The terminal end of the apparatus 20 has a receiving means 29 which is adapted to reversibly receive the block 23. In a preferred embodiment, the receiving means 29 is comprised of a substantially parallel walls 27 having a grip means 28 associated therewith to maintain the position of the block 23 in place when attached to the receiving means 29. The grip means 28 may be one of several alternate designs. For example, the block 23 may have a ridge or indentation 30 which runs along the lateral exterior surface of the block 23 and fits conformingly in a groove or ridge 31 formed in the interior face of the wall 27.

The particular examples set forth herein are instructional and should not be interpreted as limitations on the applications to which those of ordinary skill are able to apply this invention. Modifications and other uses are available to those skilled in the art which are encompassed within the spirit of the invention as defined by the scope of the following claims.

The invention claimed is:

1. A device to facilitate a surgical procedure on a heart, said device comprising:
    a main body having an outer surface and an inner surface, said outer and inner surfaces opposing one another, said main body further comprising a bottom surface disposed transversely to bottom ends of said inner and outer surfaces, extending between and connecting said inner and outer surfaces at said bottom ends;
    at least one suction port extending between said opposing inner and outer surfaces, opening through said bottom surface and adapted to engage a surface of the heart such that at least a portion of the surface of the heart becomes fixed relative to said main body, wherein said inner surface is configured to define a working space above the surface of the heart when said bottom surface of said main body is fixed thereto;
    a sealed, airtight, pressure conducting chamber within said main body, adapted to be operably connected to a source of negative pressure to conduct the negative pressure to at least one of said at least one suction ports;
    at least one passage interconnecting at least one of said at least one ports with said pressure conducting chamber; wherein each said passage has a diameter smaller than a diameter of each said port, respectively; and
    at least one instrument guide defining at least one instrument path traversing across both said inner and outer surfaces, through a wall formed by said opposing outer and inner surfaces, and through which a surgical instrument may be introduced for controlled manipulation in the working space relative to said main body.

2. The device of claim 1, wherein said at least one suction port comprises a plurality of suction ports.

3. The device of claim 2, wherein said plurality of suction ports are configured to engage the surface of the heart at multiple locations over the surface of the heart proximate to a target region.

4. The device of claim 2, wherein said sealed, airtight, pressure conducting chamber is adapted to conduct the negative pressure to said plurality of suction ports.

5. The device of claim 2, wherein at least two of said suction ports are each connected to an independent suction line, respectively.

6. The device of claim 1 wherein said main body comprises a housing forming at least a partial annular ring.

7. The device of claim 6, wherein each said suction port is contained within said housing between said opposing inner and outer surfaces, and each said suction port opens through said bottom surface.

8. The device of claim 6, wherein said housing forms a complete annular ring, said device comprising a plurality of ports spaced about said annular ring formed at said bottom surface of said housing.

9. The device of claim 6, wherein said housing is open at the top, permitting visualization of a distal end of each surgical instrument after insertion through each said instrument guide.

10. The device of claim 6, wherein said housing is dome-shaped.

11. The device of claim 10, wherein said device comprises a plurality of ports spaced about said annular ring formed at said bottom surface of said housing.

12. The instrument of claim 1, wherein said each said passage connects with each said port, respectively, such that at least one of said passages is oriented off-center to a center of said port to which it respectively connects.

13. The device of claim 6, wherein said bottom surface is substantially flat.

14. The device of claim 6, wherein said bottom surface is contoured corresponding to an expected contour of the surface of the heart to be engaged.

15. The device of claim 6, further comprising a contact layer attached to said bottom surface, wherein each of said at least one ports disposed around a periphery of said bottom surface of said housing opens through said contact layer.

16. The device of claim 15, wherein said contact layer is adapted to cushion contact between said device and the surface of the heart.

17. The device of claim 15, wherein said contact layer is adapted to facilitate formation of a tight seal between said device and the surface of the heart under negative pressure applied through said at least one port.

18. The device of claim 1, wherein at least one of said at least one instrument guides comprises a flexible shaft fixed to said main body and extending transversely to said outer surface of said main body and adapted to facilitate introduction of at least one of an instrument and a member associated with an instrument therethrough, such that said shaft can be oriented in a fashion to direct the at least one of the instrument and member associated with the instrument to a desired point within said device.

19. The device of claim 1, wherein at least one of said at least one instrument guides comprises a rigid shaft fixed to said main body and adapted to facilitate introduction of at least one of an instrument and a member associated with an instrument therethrough.

20. The device of claim 1, wherein at least one of said at least one instrument guides comprises a shaft fixed to said main body and adapted to facilitate introduction of at least one of an instrument and a member associated with an instrument therethrough, said shaft further comprising an inlet connectable to said sealed, airtight, pressure conducting chamber for fluidly connecting said pressure conducting chamber with the source of negative pressure.

21. The device of claim 1, further comprising a stop configured to limit a distance by which an instrument may be inserted through said instrument guide.

22. The device of claim 1, wherein said at least one instrument path is defined in a direction transverse to a direction in which said at least one suction port faces.

23. The device of claim 18, wherein at least one of said flexible shafts comprises a stop member that is configured to prevent passage of a stop on the instrument or member associated with the instrument to maintain a predetermined distance between the instrument or member associated with the instrument and the heart.

24. The device of claim 19, wherein at least one of said rigid shafts comprises a stop member that is configured to prevent passage of a stop on the instrument or member associated with the instrument to maintain a predetermined distance between the instrument or member associated with the instrument and the heart.

25. In combination, a device to facilitate a procedure on a heart, having a main body having at least one suction port adapted to engage a surface of the heart such that at least a portion of the surface of the heart becomes fixed relative to said main body, said main body defining an interior working space that is not placed under suction when said at least one suction port is engaged with the surface of the heart by applying suction through said at least one suction port, and at least one instrument guide defining at least one instrument port formed in a wall of said main body, transverse to a direction in which said at least one suction port faces, and through which a surgical instrument may be introduced into said interior working space for controlled manipulation relative to said main body; and at least one surgical instrument extending through said at least one instrument guide.

26. The combination of claim 25, wherein at least one of said at least one surgical instruments comprises a viewing device.

27. The combination of claim 25, wherein at least one of said at least one surgical instruments is selected from at least one of the following: a cutting apparatus, visual means, suturing instruments, suction apparatus, blowing apparatus and irrigation apparatus.

28. The combination of claim 25, wherein a plurality of instrument guides are provided in said main body.

29. The combination of claim 28, further comprising a plurality of instruments extending through said plurality of instrument guides, respectively.

30. The combination of claim 29, wherein said plurality of instruments includes at least one video scope.

31. The combination of claim 29, wherein said plurality of instruments comprises a video scope and a cutting instrument.

32. The combination of claim 29, wherein said plurality of instruments comprises a video scope and a suturing instrument.

33. A method of performing a procedure on cardiac tissue, said method comprising the steps of:
contacting a device to the cardiac tissue;
applying suction through the device to engage the cardiac tissue contacted with the device, wherein the device defines a working space relative to an inner surface of the device and a surface of the cardiac tissue that does not have suction applied thereto; and
inserting an instrument into the working space through an instrument path established through, in a direction across, a wall formed by an outer surface and the inner surface of a portion of the device.

34. The method of claim 33, wherein the instrument is a cutting instrument, said method further comprising cutting the cardiac tissue, said instrument being guided by said device during said cutting.

35. The method of claim 34, further comprising inserting a viewing scope through a second instrument path that passes through the wall of a portion of the device.

36. The method of claim 35, further comprising viewing said cutting through said viewing scope.

37. The method of claim 33, wherein the instrument is a viewing scope, said method further comprising viewing the cardiac tissue through said viewing scope, said viewing scope being guided by said device during said viewing.

38. The method of claim 33, wherein the instrument path runs transversely to a direction in which the suction is applied to the cardiac tissue.

39. In combination, a device to facilitate a procedure on a heart, having a main body having at least one suction port adapted to engage a surface of the heart such that at least a portion of the surface of the heart becomes fixed relative to said main body, and a plurality of instrument guides defining instrument paths through which surgical instruments may be introduced for controlled manipulation relative to said main body; and a plurality of surgical instruments extending through said plurality of instrument guides, wherein said plurality of instruments comprises a video scope and a suturing instrument.

40. A device to facilitate a surgical procedure on a heart, said device comprising:

a main body having an outer surface and an inner surface, said outer and inner surfaces opposing one another and defining a width of said main body wall, said main body further comprising a bottom surface disposed transversely to bottom ends of said inner and outer surfaces, extending between and connecting said inner and outer surfaces at said bottom ends;

at least one suction port extending between said opposing inner and outer surfaces, opening through said bottom surface and adapted to engage a surface of the heart such that at least a portion of the surface of the heart becomes fixed relative to said main body, wherein said inner surface is configured to define a working space above the surface of the heart when said bottom surface of said main body is fixed thereto; and at least one instrument port comprising an opening traversing said width of said main body wall and shaped to receive an instrument.

41. A device to facilitate a surgical procedure on a heart, said device comprising:

a main body having an outer surface and an inner surface, said outer and inner surfaces opposing one another and defining a width of said main body wall, said main body further comprising a bottom surface disposed transversely to bottom ends of said inner and outer surfaces, extending between and connecting said inner and outer surfaces at said bottom ends;

at least one suction port extending between said opposing inner and outer surfaces, opening through said bottom surface and adapted to engage a surface of the heart such that at least a portion of the surface of the heart becomes fixed relative to said main body, wherein said inner surface is configured to define a working space above the surface of the heart when said bottom surface of said main body is fixed thereto; and a plurality of instrument guides traversing said width of said main body wall.

* * * * *

UNITED STATES PATENT AND TRADEMARK OFFICE
CERTIFICATE OF CORRECTION

| | |
|---|---|
| PATENT NO. | : 7,485,090 B2 |
| APPLICATION NO. | : 10/946596 |
| DATED | : February 3, 2009 |
| INVENTOR(S) | : Taylor |

It is certified that error appears in the above-identified patent and that said Letters Patent is hereby corrected as shown below:

Column 1, line 65, please delete "instrument-s the" and insert --instrument fixes the--;
Column 6, line 47, please delete "suction part" and insert --suction port--.

Signed and Sealed this

Thirty-first Day of August, 2010

David J. Kappos
*Director of the United States Patent and Trademark Office*